United States Patent [19]

Brown et al.

[11] Patent Number: 4,801,574
[45] Date of Patent: Jan. 31, 1989

[54] IN-SITU ACTIVATION OF CUO/ZNO/AL₂O₃ CATALYSTS IN THE LIQUID PHASE

[75] Inventors: Dennis M. Brown, Allentown; Thomas H. Hsiung, Emmaus; Pradip Rao, Allentown; George W. Roberts, Emmaus, all of Pa.

[73] Assignee: Air Products and Chemicals, Inc., Allentown, Pa.

[21] Appl. No.: 127,830

[22] Filed: Dec. 2, 1987

[51] Int. Cl.⁴ .................. B01J 21/04; B01J 23/06; B01J 23/72; C07C 29/16
[52] U.S. Cl. .................. 502/342; 423/656; 502/30; 518/700; 518/709; 518/713
[58] Field of Search .................. 502/342, 30, 53; 518/713, 700, 709

[56] References Cited

U.S. PATENT DOCUMENTS

| | | | |
|---|---|---|---|
| 3,546,140 | 12/1970 | Gutmann et al. | 252/466 |
| 3,701,739 | 10/1972 | Bovarnick et al. | 252/454 |
| 3,850,850 | 11/1974 | Collins | 252/465 |
| 3,923,694 | 12/1975 | Cornthwaite | 252/463 |
| 4,436,833 | 3/1984 | Broecker et al. | 502/176 |
| 4,477,594 | 10/1984 | Greene et al. | 518/700 |
| 4,535,071 | 8/1985 | Schneider | 502/342 |
| 4,537,876 | 8/1985 | Blum et al. | 502/342 |
| 4,547,482 | 10/1985 | Osugi et al. | 502/208 |
| 4,567,204 | 1/1986 | Mednick et al. | 518/700 |
| 4,588,848 | 5/1986 | Butter et al. | 502/342 |
| 4,623,668 | 11/1986 | Broecker et al. | 518/709 |
| 4,639,470 | 11/1987 | Mednick et al. | 518/700 |
| 4,725,573 | 2/1988 | Hesters et al. | 518/713 |

OTHER PUBLICATIONS

Sawant et al. "In-Situ Reduction of a Methanol Synthesis Catalyst in a Three-Phase Slurry Reactor", Fuel Science & Technology Int'l.

Primary Examiner—Paul E. Konopka
Attorney, Agent, or Firm—Willard Jones, III; James C. Simmons; William F. Marsh

[57] ABSTRACT

The present invention relates to a method of activation of a CuO/ZnO/Al₂O₃ catalyst slurried in a chemically inert liquid. Successful activation of the catalyst requires the use of a process in which the temperature of the system at any time is not allowed to exceed a certain critical value, which is a function of the specific hydrogen uptake of the catalyst at that same time. This process is especially critical for activating highly concentrated catalyst slurries, typically 25 to 50 wt %. Activation of slurries of CuO/ZnO/Al₂O₃ catalyst is useful in carrying out the liquid phase methanol or the liquid phase shift reactions.

3 Claims, 1 Drawing Sheet

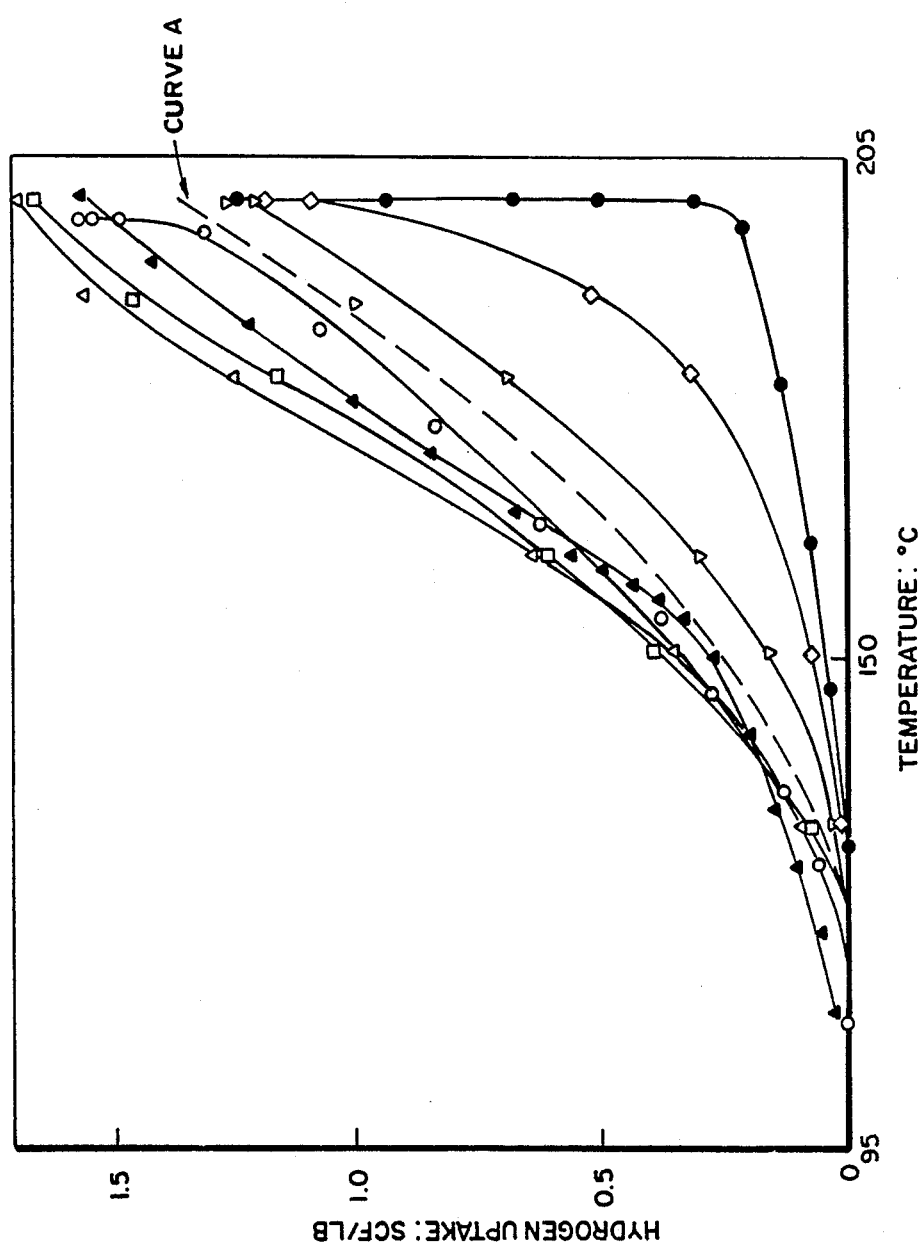

IN-SITU ACTIVATION OF CUO/ZNO/AL₂O₃ CATALYSTS IN THE LIQUID PHASE

This invention was made under DOE Contract Number DE-AC22-85PC80007 and is subject to government rights arising therefrom.

TECHNICAL FIELD

The present invention relates to a method of activation of $CuO/ZnO/Al_2O_3$ catalysts slurried in a chemically inert liquid for use in liquid phase methanol and liquid phase shift reactions.

BACKGROUND OF THE INVENTION

In the prior art, there are several minor and casual references to processes for activating $CuO/ZnO/Al_2O_3$ catalysts. Among those references having a major relationship to the activation of $CuO/ZnO/Al_2O_3$ catalysts are the following:

U.S. Pat. No. 4,623,668 discloses the preparation of methanol by catalytic conversion of a synthesis gas mixture, containing hydrogen, carbon monoxide, carbon dioxide and/or water, at 200°–320° C. and under 30—300 barr, in adiabatic and/or isothermal reactors in the presence of a catalyst containing copper and zinc, by a process in which the fresh catalyst is initially reduced with a hydrogen-containing gas, and then the synthesis is started under conventional conditions and is continued until formation of methanol in the reaction zone has declined substantially, after which the reaction is interrupted and the catalyst is regenerated.

U.S. Pat. No. 4,639,470 discloses the preparation of methanol in a liquid phase methanol reactor by entraining a methanol-forming catalyst in an inert liquid and contacting said catalyst with a synthesis gas comprising hydrogen and carbon monoxide. The mention of catalyst activation is very casual and a detailed procedure is not given, however, activation is carried out in the gas phase and the catalyst is then transferred into the liquid phase reactor.

U.S. Pat. No. 3,701,739 discloses a heterogeneous catalyst which is formed by decomposing and partially dehydrating an ammoniacal solution of a mixture of the carbonate or hydroxide of at least one metal which is reducible in hydrogen and carbonate or hydroxide of at least one metal which is nonreducible in hydrogen in a fluid bed. Residual volatiles are removed from the resulting fine particle agglomerates of the metal oxides under conditions which prevent grain growth. Afte pelletizing the composite material, it is treated with hydrogen at relatively low temperatures to reduce one or more of the oxides to its metal which remains dispersed in the remaining oxide or oxides. The catalyst thus formed has a large effective surface area and remains effective over a prolonged period of time.

U.S. Pat. No. 3,546,140 discloses a process for the preparation of a low temperature shift catalyst. The conditions for activation are disclosed in column 3 of the patent which states that "the catalyst was first reduced by treatment for about 8 hours at 500° F."

U.S. Pat. No. 3,850,850 discloses a catalyst precursor which is made by forming a first precipitate comprising oxides capable of reacting together to form a mixed oxide having a spinel structure, forming a second precipitate comprising a copper compound decomposable to oxide, and mixing the two precipitates. Such a precursor may after reduction be used as a methanol synthesis catalyst capable of long-term use at high levels of catalytic activity.

U.S. Pat. No. 4,535,071 discloses a catalyst for methanol synthesis which contains (a) as catalytically active substances copper oxide and zinc oxide, which, if desired, may be at least partially reduced and (b) as a thermal stabilizing substance aluminum oxide. The proportion of pores with a diameter of 20–75 angstroms (mesopores) is at least 20% and the proportion of pores with a diameter greater than 75 angstroms (macropores) is at the most 80%. The desired pore distribution can be obtained by using colloidally dispersed aluminum oxide or hydroxide in the production of the catalyst.

U.S. Pat. No. 4,436,833 discloses a process for the preparation of methanol by reacting a gaseous mixture of carbon monoxide, carbon dioxide and hydrogen at an elevated temperature and pressure over a catalyst which contains zinc, copper, and aluminum. The catalyst is prepared from a co-crystalline material of the formula:

$$Cu_{2.2}Zn_{2.8}(OH)_6(CO_3)_2$$

containing aluminum hydroxide as a structural promoter, by calcination and reduction from 160°–350° C. The novel catalyst has an advantage of giving a substantially increased space time yield and having a longer life.

U.S. Pat. No. 3,922,694 discloses a methanol synthesis catalyst precursor which comprises copper oxide and a support comprising spinel-forming metal oxides, spinel being present in crystallites not larger than 120 angstroms. Using catalyst prepared from such a precursor by reduction, methanol synthesis can be operated without changing catalyst for longer periods than when using a similar catalyst containing no spinel. A precipitation method for making the precursor is also disclosed.

U.S. Pat. No. 4,547,482 discloses a catalyst composition having copper oxide, zinc oxide, and an oxy-acid of phosphorus or its salt; and a method for producing methanol by reacting carbon monoxide and/or carbon dioxide with hydrogen in the vapor phase in the presence of a catalyst, wherein the catalyst is the aforesaid catalyst composition which has been activated by gas-phase reduction with a hydrogen-containing gas.

U.S. Pat. No. 4,477,594 discloses a process for the synthesis of mixtures which include saturated aliphatic alcohols. In the first step of the process, a catalyst, which comprises the oxides of copper, zinc, aluminum, potassium and one or more additional metals selected from the group consisting of chromium, magnesium, cerium, cobalt, thorium, lanthanum, is partially activated. In this step a reducing gas stream, which includes hydrogen and at least one inert gas, flows past the catalyst at a space velocity of up to 5,000 standard liters per hour, per kilogram of catalyst. The partially activated catalyst is then subjected to the second step of the activation process. In this step the catalyst is contacted by an activation gas stream comprising hydrogen and carbon monoxide present in a volume ratio of 0.5 to 1 and 4 to 1, respectively, at a temperature of 200°–450° C. and a pressure of between 35–200 atmospheres. The activation gas flows at a space velocity of about 1,000–20,000 standard liters per hour per kilogram of catalyst. Second stage activation continues until the catalyst is contacted with at least 500,000 standard liters of activation gas per kilogram of catalyst. The fully activated catalyst, in the third step of the process, contacts the synthesis gas stream comprising hydrogen and carbon monoxide.

U.S. Pat. No. 4,537,876 discloses a method for activating a methanol synthesis catalyst. In this method, the catalyst is slurried in an inert liquid and is activated by a reducing gas stream. The activation step occurs in-situ. That is, it is conducted in the same reactor as the subsequent step of synthesizing methanol from a methanol gas stream catalyzed by the activated catalyst still dispersed in a slurry.

Except for U.S. Pat. No. 4,537,876, the above references utilize a gas-phase reduction/activation step, however, all of the references share a common characteristic: there is no recognition of the relationship between the catalyst temperature and hydrogen consumption, and the criticality of this relationship in determining whether the catalyst is properly activated.

SUMMARY OF THE INVENTION

The present invention is an improvement to a process for the activation of a $CuO/ZnO/Al_2O_3$ catalyst for use in a liquid phase methanol reaction or a liquid phase shift reaction. In the activation process, the catalyst is dispersed in an inert liquid phase medium thereby producing a catalyst slurry and is activated by subjecting the catalyst slurry to a temperature ramping in the presence of a hydrogen containing atmosphere. The improvement comprises controlling activation temperature during the temperature ramping over the range of 110° C. to 200° C. in relation to hydrogen consumption, whereby in controlling the temperature ramping, a specific activation temperature in the temperature ramping is maintained prior to being increased according to the temperature ramping until at least a minimal hydrogen uptake has been achieved. The minimal hydrogen uptake is ascertained by the following equation:

$$H_2 \text{ Uptake} \geq \chi(9.3 - 0.16[T] + .00069[T^2])$$

wherein $H_2$ Uptake has units of SCF/lb of catalyst, $\chi$ is the weight fraction of copper in the catalyst, and $T$ is the specific activation temperature in degrees Centigrade.

The method of the present invention is particularly beneficial for dense catalyst concentrations, i.e. in the range of 25 to 50 wt %.

BRIEF DESCRIPTION OF THE DRAWING

The single FIGURE of the drawing is a plot of hydrogen uptake versus temperature for several temperature ramping activation methods.

DETAILED DESCRIPTION OF THE INVENTION

Commercial methanol synthesis catalysts and low-temperature-shift catalysts are often based on the $CuO/ZnO/Al_2O_3$ system. Activation of these catalysts requires the reduction of the copper from a high oxidation state to lower oxidation states. In conventional gas phase reactors with fixed catalyst beds, the procedures for carrying out this reduction or activation are well established. In liquid phase reactors, such as those used in liquid phase methanol and liquid phase shift processes, the catalyst is suspended in an inert liquid during operation. The most efficient and economical way to activate the catalyst prior to beginning liquid phase operation is to reduce the catalyst after it has been suspended in the liquid, a technique which is referred to as "in-situ" activation.

Activating the catalyst in the presence of a liquid has proven to be a significant technical challenge. Catalyst loadings can vary in a liquid phase reactor over a range from about 5 wt % catalyst to about 50 wt % catalyst. As the catalyst loading is varied, slurry properties, such as slurry viscosity, may change drastically to further complicate the activation process. Prior to the development of the present method unsuccessful catalyst activations were often experienced, particularly for high catalyst loadings both in the laboratory and in large pilot plants. By unsuccessful activation it is meant that the full activity of the catalyst has not been achieved at the end of the activation process. Moreover, no remedial procedure could be found that would successfully complete the activation process, i.e. achieve full catalyst activity, if the initial attempt at activation was unsuccessful.

As mentioned earlier, initial attempts at in-situ activation of $CuO/ZnO/Al_2O_3$ catalyst slurries were based on established procedures for activating these catalysts in conventional gas phase reactors. In a conventional gas phase fixed bed reactor, the catalyst activation is accomplished by very careful control of the reductant concentration and reactor temperature. Normally, a procedure typically starts with a low hydrogen concentration, e.g. 0.3 vol %, and a low reactor temperature, e.g. 120° C., and may end up with a high hydrogen concentration, e.g. 10 vol %, and a high reactor temperature, e.g. 250° C.

For in-situ activation of a methanol catalyst, where the catalyst is slurried in an inert oil, U.S. Pat. No. 4,537,876 studied various activation methods in well mixed autoclaves. The patent discloses varied process parameters including temperature, pressure, and reductant gas compositions. The conclusions were that the best activation conditions are a pressure of 875 kPa, final temperatures of 220°–240° C., and a hydrogen/nitrogen mixture comprised of hydrogen from 2–25 vol %, and an activation gas flow rate of 1,000 liters per hour per kilogram of catalyst.

These studies in U.S. Pat. No. 4,537,876 were carried out with dilute slurries, i.e. 5–25 wt %. As disclosed in the patent, it was found that the adjustment of activating gas flow rate was all that was necessary to successfully activate the catalyst in a stirred autoclave. However, this method has been found to be unsuccessful in achieving activation in other reactor systems. This is particularly true when the slurry concentration is higher as is consistent with commercial targets, and with larger, e.g. pilot plant, reactors.

The present invention is an improvement in the method for in-situ activation of $CuO/ZnO/Al_2O_3$ catalysts such as those for methanol synthesis and low temperature shift. The present invention is based on extensive experimentation during which methanol synthesis and shift catalysts were activated in-situ under a variety of operating conditions, e.g. gas flow rate, hydrogen concentration, rate of temperature increase, etc. In each experiment, the catalyst slurry was heated from room temperature to a final temperature of about 240° C. while a mixture of hydrogen in nitrogen was passed through the slurry. The amount of hydrogen consumed by the catalyst was constantly measured by measuring the inlet and outlet flow rates and the inlet and outlet hydrogen concentrations. Examples for a typical methanol catalyst are shown in the single figure of the drawing. The figure shows the specific hydrogen uptake (SCF of hydrogen consumed per pound of catalyst) at various reactor temperatures. Several different activations are shown. Four of these were successful in that the subsequent methanol activity was high, but three of the activations were failures resulting in unsatisfactory methanol activity.

Inspection of the operating lines in the figure show that there were two distinct regimes; one for successful and the other for unsuccessful activation. An empirical curve dividing these two regimes is shown as Curve A on the figure. Any activation process which produces an operating line or trajectory that falls totally above curve A will result in successful catalyst activation. An activation process whose trajectory makes substantial penetration into the region below curve A will result in unsuccessful activation. Curve A, which describes the relationship determining the minimal specific hydrogen uptake required for successful activation of the catalyst at a given temperature before the temperature is increased per the activation method, is expressed by the following equation:

$$H_2 \text{ Uptake} \geq \chi(9.3 - 0.16[T] + .00069[T^2]) \quad (1)$$

wherein $H_2$ Uptake has units of SCF/lb of catalyst, $\chi$ is the weight fraction of copper in the catalyst, and T is the specific activation temperature in degrees Centrigrade.

Data from the seven activations shown in the figure are presented in Table I, showing the basis for judging whether the catalyst has been successfully activated.

TABLE 1

Results of In-Situ Activation of a Methanol Catalyst

| Experiment Number | Final Catalyst Activity: (gmole/kg/hr) | Specific Hydrogen Uptake at 200° C.: SCF/lb | Activation Successful |
|---|---|---|---|
| 1 | 16.7 | 1.68 | Yes |
| 2 | 16.5 | 1.65 | Yes |
| 3 | 16.4 | 1.54 | Yes |
| 4 | 16.5 | 1.45 | Yes |
| 5 | 8.0 | 1.18 | No |
| 6 | 14.9 | 1.06 | No |
| 7 | 8.4 | 1.05 | No |

The final activity of all four of the successfully activated catalysts is 16–17 gm-moles $CH_3OH$/hr per kilogram catalyst at 250° C., 750 psig and a CHSV of 5,000 standard liters per hour per kilogram of catalyst with a feed gas consisting of 51 vol % CO, 35 vol % $H_2$, 13 vol % $CO_2$ and 1 vol % $N_2$. Conversely, the final activity of all three unsuccessfully activated catalysts is substantially below this value. Note that the specific hydrogen uptake at 200° C. is a good indicator of successful activation. In all cases where the specific hydrogen uptake was greater than 1.4 standard cubic foot of hydrogen per pound of catalyst (87.5 1-$H_2$/kg-cat), the activation was successful. When the catalyst activation was unsuccessful, the specific hydrogen uptake was less than 1.2 standard cubic feet of hydrogen per pound of catalyst (75 1-$H_2$/kg-cat).

Equation (1) can be used as the basis for a control system to insure successful in-situ catalyst activation. For example, the cumulative hydrogen consumption (and specific hydrogen uptake) may be used as a basis for controlling the rate at which the temperature of the system is increased. Starting with the system at a low temperature, e.g. 120° C., activating gas containing, e.g. 2–10% hydrogen, is introduced. The hydrogen is slowly consumed by the catalyst, but the temperature is not raised (to speed up the activation process) until the measured hydrogen consumption is equal to or above the minimum amount as determined by Equation (1). The temperature is then increased slowly and the specific hydrogen uptake is periodically measured. It is best in practice for the initial heating rate to be less than 10° C. per hour. As activation proceeds, the temperature is raised only when the hydrogen consumption is equal to or above the minimum amount determined by Equation (1). At any point in the activation, if the specific hydrogen uptake approaches the minimum specific hydrogen uptake too closely, the rate of increase in reactor temperature is decreased or reactor heating is discontinued all together. This is done to prevent the catalyst from becoming overheated, i.e. in the figure, preventing the trajectory of the activation from falling below Curve A, which would irreveresibly lower the final activity of the catalyst. If the specific hydrogen uptake rises substantially above the minimum, the rate of reactor heating should be increased to reduce the total time required for catalyst activation.

Other system parameters may also be used in this control strategy. Examples of these are raising the system pressure, raising the activation gas flow rate, and raising the hydrogen concentration; these all will serve to increase the rate of specific hydrogen uptake. Thus, one or more of these variables may be increased as an alternative to or as a supplement to reducing the rate of temperature increase.

Based on the above information, the step-by-step procedure for controlling activation of a commercial $CuO/ZnO/Al_2O_3$ catalyst is as follows: preliminaries to this procedure involve setting of the system pressure for activation and making ready of the proper mix of hydrogen and nitrogen for activation. Use of higher pressures than ambient is preferred to maximize gas throughout while minimizing catalyst carryover. A typical gas blend would be 2% hydrogen, 98% nitrogen. However, higher hydrogen concentrations could also be used without endangering the control over system temperature due to the excellent heat transfer characteristics of liquid phase reactors. Control of system temperature is important due to the exothermicity of the reduction reaction and the deleterious effect of high temperatures on final catalyst activity. The steps are: (1) pressurize reactive system with pure nitrogen to desired activation pressure; (2) begin mixing/circulating the catalyst slurry; (3) as the slurry is being mixed/circulated, heat the reactor to 110° C. under a steady nitrogen flow, upon achieving 110° C., start the activating gas blend and monitor inlet and outlet hydrogen concentrations and gas flows rates; (4) determine cumulative hydrogen consumption, calculate the specific hydrogen uptake and compare it with the minimum specific hydrogen uptake (Equation (1)) for that temperature. If the uptake is below the minimum, hold the reactor temperature constant until the uptake is at least equal to the minimum; (5) after achieving at least the minimum, raise the reactor temperature at a rate of approximately 10° C. per hour making sure that at all times the specific hydrogen uptake stays above the reference curve; (6) advance system temperature in this way until a temperature of 200° C. is reached; (7) once a temperature of 200° C. is reached, hold for several hours to insure that the reduction is complete; and (8) raise the temperature to 240° C. at about 10° C./hour, checking for further hydrogen uptake. After one (1) hour at 240° C., the activation is complete.

As one can see, the present invention is a method that uses a predetermined relationship between specific hydrogen uptake as a function of temperature as the control for catalyst activation. Use of the method of the present invention requires that hydrogen concentration exiting the reactor and entering the reactor is monitored. From this concentration difference, the gas flow rate and the known weight of the catalyst in the reactor, a specific hydrogen uptake can be calculated. This calculated hydrogen uptake is then compared with the minimal hydrogen uptake as determined by Equation (1). If the calculated hydrogen uptake is equal to or greater than the minimal hydrogen uptake, the process temperature ramping can proceed at regular rates, e.g. 10° C. per hour. If the calculated hydrogen uptake is less than the minimal hydrogen uptake for the activation temperature, the temperature ramping has to be delayed until the hydrogen uptake catches up with and then exceeds the minimal value for that temperature. The temperature ramping should be modified if hydrogen uptake at any time slows down or stops which is possible, because if one continues the temperature advance it would only take the hydrogen uptake below the minimum level set by Equation (1).

Therefore, in conclusion, it has been shown that temperature control during catalyst activation is critical, particularly in systems with high catalyst loadings. Unlike conventional methods, the present invention is based on the use of hydrogen consumption or uptake as the guide for temperature control. As the hydrogen consumption is based on the unit weight of catalyst, the present activation procedure does not depend upon catalyst loading.

The present invention has been described with reference to some embodiments thereof, these embodiments, should not be taken as a limitation on the present invention. Any limitation of the present invention should be ascertained from the following claims:

We claim:

1. In a process for the activation of $CuO/ZnO/Al_2O_3$ catalysts, which are used as a catalyst for liquid phase methanol synthesis reaction or liquid phase shift reaction, wherein said catalyst is dispersed in an inert liquid phase medium thereby producing a catalyst slurry and activated by subjecting the catalyst slurry to a temperature ramping in the presence of a hydrogen containing atmosphere, the improvement for achieving full activity of the catalyst comprises:
   (a) controlling activation temperature during the temperature ramping over the range of 110° C. to 200° C. in relation to hydrogen consumption, wherein in controlling the temperature, a specific activation temperature in the temperature ramping is maintained prior to being increased according to the temperature ramping until at least a minimal hydrogen uptake has been achieved: said minimal hydrogen uptake being ascertained by the following equation:

$$H_2 \text{ Uptake} \geq \chi(9.3 - .16[T] + 0.00069[T^2])$$

wherein $H_2$ Uptake has units of SCF/lb of catalyst, $\chi$ is the weight fraction of copper in the catalyst, and T is the specific activation temperature in degrees Centrigrade;
   (b) holding the temperature at 200° C. for an effective period of time so as to insure that the reduction is complete; and
   (c) raising the temperature from 200° C. to 240° C. at about 10° C./hour and holding the temperature at 240° C. for one (1) hour, thereby completing the activation of the $CuO/ZnO/Al_2O_3$ catalyst.

2. The process of claim 1 further comprises raising pressure, increasing the hydrogen containing atmosphere flow rate, increasing hydrogen concentration of the hydrogen containing atmosphere or combinations thereof in order to increase hydrogen uptake at a particular temperature.

3. The process of claim 1 wherein said catalyst slurry has a catalyst concentration in the range of 25 to 50 wt %.

* * * * *